(12) United States Patent
Bogin et al.

(10) Patent No.: US 10,022,397 B2
(45) Date of Patent: Jul. 17, 2018

(54) TREATMENT OF RHEUMATOID ARTHRITIS USING NOBLE GAS MIXTURES

(71) Applicant: Nobilis Therapeutics, Inc., Portland, OR (US)

(72) Inventors: Vlad Bogin, Portland, OR (US); Thomas Ichim, San Diego, CA (US)

( * ) Notice: Subject to any disclaimer, the term of this patent is extended or adjusted under 35 U.S.C. 154(b) by 0 days.

(21) Appl. No.: 15/628,371

(22) Filed: Jun. 20, 2017

(65) Prior Publication Data
US 2017/0360828 A1    Dec. 21, 2017

Related U.S. Application Data

(60) Provisional application No. 62/352,497, filed on Jun. 20, 2016.

(51) Int. Cl.
*A61K 33/00*    (2006.01)

(52) U.S. Cl.
CPC ............................. *A61K 33/00* (2013.01)

(58) Field of Classification Search
CPC ........................................................ A61K 33/00
See application file for complete search history.

(56) References Cited

U.S. PATENT DOCUMENTS

| | | | | |
|---|---|---|---|---|
| 5,733,572 A * | 3/1998 | Unger | ....................... | A61K 8/14 424/1.21 |
| 7,390,508 B2 * | 6/2008 | Franks | .................... | A61K 33/00 424/600 |
| 8,632,821 B2 * | 1/2014 | Bessiere | ................. | A61K 33/00 424/613 |
| 2010/0303918 A1 * | 12/2010 | Watson | ................. | A61K 9/0078 424/489 |
| 2012/0039884 A1 * | 2/2012 | Watson | ................. | A61K 9/0009 424/134.1 |
| 2013/0302445 A1 * | 11/2013 | Barbut | .................. | A61K 9/0043 424/700 |

FOREIGN PATENT DOCUMENTS

| WO | WO 2008132176 A2 * | 11/2008 | ........... C12Q 1/6883 |
|---|---|---|---|
| WO | WO 2014145443 A2 * | 9/2014 | ............. A61K 47/02 |

* cited by examiner

*Primary Examiner* — Robert A Wax
*Assistant Examiner* — Olga V Tcherkasskaya
(74) *Attorney, Agent, or Firm* — Baumgartner Patent Law; Marc Baumgartner

(57) ABSTRACT

The invention disclosed provides means of inhibiting, ameliorating, and/or treatment of rheumatoid arthritis through the use of Noble gas containing mixtures. In one embodiment, the invention provides means of reducing inflammation and immune associated pathology through administration of Noble gas mixtures. In one specific embodiment, Xenon gas is administered to a patient in need at concentrations and frequencies sufficient to inhibit inflammatory and autoimmune processes. In another embodiment Noble gas mixtures are administered to reduce pain and provide symptomatic relieve to a patient suffering from rheumatoid arthritis. In another embodiment the use of Noble gas containing mixtures is disclosed as a means of reducing joint destruction through inhibition of matrix metalloprotease production and activity.

9 Claims, No Drawings

TREATMENT OF RHEUMATOID ARTHRITIS USING NOBLE GAS MIXTURES

CROSS-REFERENCE TO RELATED APPLICATIONS

The present invention claims priority to U.S. Provisional Application No. 62/352,497, filed Jun. 20, 2016, which is hereby incorporated in its entirety including all tables, figures, and claims

FIELD OF THE INVENTION

The invention pertains to the field of autoimmunity, more specifically, the invention pertains to the use of utilization of Noble gases to treated rheumatoid arthritis, more specifically the invention pertains to the use of gaseous compositions, in some embodiments, xenon-gas containing composition to reduce pain and inflammatory/autoimmunity processes subside.

BACKGROUND

Autoimmune diseases are characterized by an excessive reaction of the immune system against endogenous tissue. The immune system erroneously recognizes endogenous tissue as foreign bodies to be combated. This results in severe inflammatory reactions, which lead to damage to organs affected by them. An important part in distinguishing between endogenous and exogenous structures is played by T lymphocytes or T cells, which are "trained" in the thymus to dock only onto endogenous cell surface molecules, the so-called MHC molecules, and thus to tolerate endogenous structures. These processes are called "clonal deletion" and "clonal selection". During the initial selection in the thymus, only those T cells, which are able to recognize MHC molecules on the endogenous cell membranes survive, while the binding is however not so strong that it could lead to activation of the T cells. T cells which cannot bind to or recognize endogenous MHC molecules at all are eliminated. In the clonal deletion also taking place in the thymus, those T cells which are able to "unerringly" recognize and strongly bind endogenous MHC molecules in such a manner that they would be activated, which would in the end lead to the destruction of endogenous cells, are eliminated. This process is one of those measures which the immune system takes in order to be able to protect the "self" and combat the "exogenous".

In autoimmune diseases, a group of the T cells behaves abnormally. In addition to the still functioning defence from exogenous molecules and organisms, they now also attack endogenous structure. Organs or tissues are perceived as exogenous. There can be various consequences: if vital structures are affected, an autoimmune disease will take a fatal course. The immune system directs its defence against these structures, cellular and also humoral defence reactions are set in motion, and autoantibodies are formed, as a result of which the organs affected in the course of time cease to function. Most commonly, the immune system is weakened and the body becomes susceptible to all kinds of diseases. Under some circumstances, recognition of the exogenous is also disrupted, and as a result the spreading of degenerated cancer cells can no longer be effectively prevented, and those affected are more susceptible to infectious diseases. In the course of the disease, cells of the immune system destroy the endogenous structures, while the body's repair mechanisms attempt as far as possible to regenerate the damaged organ parts. As a rule, without treatment this erroneous attack of the defensive system continues throughout life or until the complete destruction of the target structure. Autoimmune diseases are treated according to the organ affected. In this, the basic principle of the causal therapy is to suppress the activity of the immune system by administration of immunosuppressants, e.g., cortisone. These substances are characterized by multiple systemic side-effects and interactions, owing to which attempts have been made to develop new drugs which specifically influence the mechanisms involved in the disease event. Examples of this are natalizumab and infliximab. Natalizumab is a monoclonal antibody and selective inhibitor of IgG4, an adhesion molecule which is located on the surface of white blood cells. Natalizumab inhibits the migration of white blood cells into inflammation foci and is used for the treatment of particularly aggressive forms of plaque progressive multiple sclerosis. Infliximab is a chimeric monoclonal antibody against tumour necrosis factor .alpha. (TNF.alpha.), which plays a key part in autoimmune inflammatory reactions. Infliximab is used in rheumatoid arthritis, Crohn's disease, and psoriasis.

SUMMARY OF THE INVENTION

Certain embodiments of the teachings herein are directed to methods of inhibiting an autoimmune process, such as rheumatoid arthritis, comprising the steps of: a) obtaining a patient suffering from a pathological immune response against self-antigens; b) providing to said patient a Noble gas composition; and c) adjusting dosage and frequency of administration of said Noble gas composition based on immunological and/or clinical response.

Various aspects of the invention relating to the above are enumerated in the following paragraphs:

Aspect 1. A method of inhibiting an autoimmune process comprising the steps of: a) obtaining a patient suffering from a pathological immune response against self-antigens; b) providing to said patient a Noble gas composition; and c) adjusting dosage and frequency of administration of said Noble gas composition based on immunological and/or clinical response.

Aspect 2. The method of aspect 1, wherein said autoimmune process is rheumatoid arthritis.

Aspect 3. The method of aspect 2, wherein said rheumatoid arthritis patient is defined as suffering from at least one symptom of rheumatoid arthritis, the symptom selected from the group consisting of morning stiffness, painful joints, swollen joints, loss of grip strength, and pain.

Aspect 4. The method of aspect 1, wherein said autoimmune process is selected from a group comprising of: multiple sclerosis, rheumatoid arthritis, type 1 diabetes, Crohns disease, ulcerative colitis, psoriasis, celiac disease, Acute disseminated encephalomyelitis (ADEM), Addison's disease, A gammaglobulinemia, Alopecia areata, Amyotrophic lateral sclerosis, Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune uveitis, Behcet's disease, Celiac disease, Cold agglutinin disease, Crohn's disease, Dermatomyositis, Dermatomyositis, Eosinophilic fasciitis, Goodpasture's syndrome, Graves' disease, Guillain-Barre syndrome (GBS), Hashimoto's encephalopathy, Hashimoto's thyroiditis, Idiopathic thrombocytopenic purpura, Lupus erythematosus, Miller-Fisher syndrome, Mixed connective tissue disease, Myasthenia gravis, Narcolepsy, Pemphigus vulgaris, Pernicious anaemia, Polymyositis Primary biliary cirrhosis, Psoriasis, Psoriatic arthritis, Relapsing polychondritis, Rheumatic fever, Sjogren's syndrome, Temporal arteritis, Transverse myelitis, Ulcerative colitis, Undifferentiated connective tissue disease, Vasculitis, and Wegener's granulomatosis.

Aspect 5. The method of aspect 1, wherein said Noble gas mixture contains oxygen and a proportion by volume of 20 to 70% of xenon.

Aspect 6. The method of aspect 5, wherein said proportion of xenon is between 22 and 60% by volume to oxygen.

Aspect 7. The method of aspect 6, wherein said proportion of xenon is between 25 and 60% by volume to oxygen.

Aspect 8. The method of aspect 1, wherein said noble gas containing mixture consists only of a) oxygen and xenon or b) air and xenon.

Aspect 9. The method of aspect 1, wherein said noble gas containing mixture also contains nitrogen, helium, Nitric Oxide, krypton, argon or neon.

Aspect 10. The method of aspect 1, wherein said noble gas containing mixture contains a proportion by volume of oxygen of between 15 and 25%.

Aspect 11. The method of aspect 1, wherein said noble gas containing mixture is supplied for inhalation from a pressurized container at a pressure greater than 2 bar.

Aspect 12. The method of aspect 1, wherein said noble gas containing mixture is administered intranasally.

Aspect 13. The method of aspect 1, wherein said noble gas containing mixture is administered through the use of a hyperbaric chamber.

Aspect 14. The method of aspect 13, wherein said hyperbaric chamber is pressurized to a pressure of no more than 3 atm (0.3 MPa).

Aspect 15. The method of aspect 14, wherein a noble gas is administered to the patient while the patient is in the hyperbaric environment.

Aspect 16. The method of aspect 1 wherein said noble gas is administered by inhalation or simulated inhalation.

Aspect 17. The method of aspect 1, wherein said noble gas is xenon, helium, or a mixture of xenon and helium.

Aspect 18. The method of aspect 1, wherein the noble gas is xenon or a mixture of xenon and helium, and the partial pressure of xenon is no more than about 0.8 atm (0.08 MPa).

Aspect 19. The method of aspect 1, wherein said noble gas is administered mixed with air, the air partial pressure being about 1 atm (0.1 MPa).

Aspect 20. The method of aspect 1, wherein said noble gas is administered as part of a gas mixture comprising oxygen, the nitrogen partial pressure in the mixture being equal to or less than about 0.8 atm (0.08 MPa).

Aspect 21. The method of aspect 20, wherein said gas mixture is essentially free of nitrogen.

Aspect 22. The method of aspect 21, wherein the oxygen partial pressure is about 0.2 atm (0.02 MPa).

Aspect 23. The method of aspect 1, wherein said clinical assessment is performed by the EULAR score.

Aspect 24. The method of aspect 1, wherein said immunological assessment is performed by quantification of levels of inflammatory markers.

Aspect 25. The method of aspect 24, wherein said inflammatory marker is CRP.

Aspect 26. The method of aspect 24, wherein said inflammatory marker is IL-1.

Aspect 27. The method of aspect 24, wherein said inflammatory marker is IL-6.

Aspect 28. The method of aspect 24, wherein said inflammatory marker is IL-8.

Aspect 29. The method of aspect 24, wherein said inflammatory marker is IL-17.

Aspect 30. The method of aspect 24, wherein said inflammatory marker is TNF-alpha.

Aspect 31. The method of aspect 24, wherein said inflammatory marker is HMGB -1.

Aspect 32. The method of aspect 24, wherein said inflammatory marker is IL-33.

Aspect 33. A method increasing sensitivity to an anti-cytokine biologic in a rheumatoid arthritis patient, said method comprising administration of a Noble gas containing mixture.

Aspect 34. A method of inducing antigen specific tolerance, said method comprising generation of a particle containing a Noble gas together with an antigen to which tolerance is desired.

Aspect 35. A method of reducing pain in a patient with rheumatoid arthritis comprising administration of a therapeutically sufficient concentration and frequency of a Noble gas.

DETAILED DESCRIPTION OF THE INVENTION

The invention teaches the counterintuitive findings that xenon administration induces an increase in anti-inflammatory/immune modulatory processes that are useful in the treatment of, and/or amelioration of rheumatoid arthritis. Rheumatoid arthritis (RA) is an autoimmune condition characterized by adaptive immune autoreactivity leading to chronic inflammation of the synovium and the presence of rheumatoid arthritis synovial fibroblasts (RASFs) that undergo hyperplasia and invade cartilage and bone [1]. RASFs exhibit an increased ability to enter into the cell cycle, resulting in hyperplasia [2], and also show a decreased ability to undergo apoptosis [3]. RASFs produce proinflammatory cytokines, such as IL-1 and TNF-α which provide further stimulation for the ongoing inflammation[4]. Furthermore, enzymes including stromelysin and collagenase are produced and are capable of invading cartilage and bone [5].

Clinically, RA affects approximately 0.5-1% of the global population [6] with varying degrees of severity. The typical treatment algorithm involves initiation of NSAIDS, however more recent practice has been concurrent initiation of disease modifying antirheumatic drugs (DMARDs). These agents are slow acting but have been demonstrated to inhibit radiological progression of RA. Such agents typically include: 1) hydroxychloroquine, which acts in part as a toll like receptor (TLR) 7/9 antagonist, thus decreasing innate immune activation [7]; 2) Leflunomide, an antimetabolite that inhibits pyrimidine synthesis and protein tyrosine kinase activity [8], which results in suppression of T cell responses [9], and has been also demonstrated to inhibit dendritic cell (DC) activation [10]; 3) Injectable gold compounds such as auranofin which directly or through metabolites such as dicyanogold(i) have been demonstrated to inhibit T cell and antigen presenting cell activation [11, 12], as well as cause Th2 deviation [13]; 4) Sulfasalazine, was used since 1950, acts primarily through inhibition of cycloxygenase and lipoxygenase [14]; and 5) Methotrexate, an antifolate that inhibits T cell activation and proliferation, that has been one of the golden standards for RA [15]. Typically combinations of DMARDs with glucocorticoids are used, or alternatively pulse of high dose glucocorticoids are administered to cause a general inhibition of inflammation [16].

The field of RA therapy has been revolutionized by the introduction of the TNF-✓-targeting agents, Remicade, Enbrel, and Humira, sometimes referred to as "biological DMARDs." These are implemented primarily after response to conventional DMARDs has failed [17]. Although improvement in quality of life has occurred as a result of biological DMARDs, substantial progress remains to be made. For example, TNF-alpha blockers have been associated with reactivation of infectious disease, autoantibody formation and the possibility of increased lymphoma risk [18, 19]. Thus to date, one of the major limitations to RA therapy has been lack of ability to specifically inhibit autoreactive responses while allowing other immune components to remain intact.

An "autoimmune disease" herein is any non-malignant disease or disorder arising from antibodies that are produced directed against an individual's own (self) antigens and/or tissues.

"Immunosuppressive drugs" are any molecules that interfere with the immune system and blunt its response to foreign or self antigens. Cyclophosphamide (CYC) and mycophenolate mofetil (MMF) are two such kinds of molecules. This term is intended to encompass any drug or molecule useful as a therapeutic agent in downregulating the immune system. This method particularly contemplates drugs that have been used to treat autoimmune diseases such as rheumatoid arthritis, juvenile rheumatoid arthritis, systemic lupus erythematosus (SLE), lupus nephritis (LN), Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis.

Antibody "effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity; Fc receptor binding; antibody-dependent cell-mediated cytotoxicity (ADCC); phagocytosis; down regulation of cell surface receptors (e.g. B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g. Natural Killer (NK) cells, neutrophils, and macrophages) enable these cytotoxic effector cells to bind specifically to an antigen-bearing-target cell and subsequently kill the-target cell with cytotoxins. The antibodies-"arm" the cytotoxic cells and are absolutely required for such killing. The primary cells for mediating ADCC, NK cells, express Fc.gamma.RIII only, whereas monocytes express FcγRI, FcγRII and FcγRIII. FcR expression on hematopoietic cells is summarized in Table 3 on page 464 of Ravetch and Kinet, Ann. Rev. Immunol 9: 457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95: 652-656 (1998).

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass) which are bound to their cognate antigen. To assess complement activation, a CDC assay, e.g. as described in Gazzano-Santoroetal., J. Immunol. Methods 202: 163 (1996), may be performed.

The term "anti-inflammatory agent" as used herein, refers to any compound having known effectiveness to reduce symptoms of inflammation. For example, reduction in symptoms may include, but are not limited to, reduced swelling, redness and/or local lymphocyte levels. For example, an anti-inflammatory agent may include, but is not limited to, aspirin, acetominophen, ibuprofen, cortiocosterone, or cortisol.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "drug", "agent" or "compound" as used herein, refers to any pharmacologically active substance capable of being administered which achieves a desired effect. Drugs or compounds can be synthetic or naturally occurring, non-peptide, proteins or peptides, oligonucleotides, or nucleotides (DNA and/or RNA), polysaccharides or sugars.

The term "administered" or "administering", as used herein, refers to any method of providing a composition to a patient such that the composition has its intended effect on the patient. For example, one method of administering is by an indirect mechanism using a medical device such as, but not limited to a catheter, applicator gun, syringe etc. A second exemplary method of administering is by a direct mechanism such as, local tissue administration (i.e., for example, extravascular placement), oral ingestion, transdermal patch, topical, inhalation, suppository etc.

The term "patient", as used herein, is a human or animal and need not be hospitalized. For example, out-patients, and persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "pharmaceutically" or "pharmacologically acceptable", as used herein, refer to molecular entities and compositions that do not produce adverse, allergic, or other untoward reactions when administered to an animal or a human.

The term, "pharmaceutically acceptable carrier", as used herein, includes any and all solvents, or a dispersion medium including, but not limited to, water, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, and the like. Supplementary bioactive ingredients also can be incorporated into such carriers.

The term "biologically active" refers to any molecule having structural, regulatory or biochemical functions. For example, biological activity may be determined, for example, by restoration of wild-type growth in cells lacking protein activity. Cells lacking protein activity may be produced by many methods (i.e., for example, point mutation and frame-shift mutation). Complementation is achieved by transfecting cells which lack protein activity with an expression vector which expresses the protein, a derivative thereof, or a portion thereof.

In one aspect of the invention, Noble gas mixtures are administered to treat autoimmunity. Further, it is preferable if the autoimmune disease is selected from the group consisting of: type I diabetes mellitus, rheumatoid arthritis, multiple sclerosis, chronic gastritis, Crohn's disease, Basedow disease, Bechterew disease, psoriasis, myasthenia gravis, autoimmune hepatitis, APECED, Chrug-Strauss syndrome, ulcerative colitis, glomerulonephritis, Guillain-Barre syndrome, Hashimoto thyroiditis, lichen sclerosus, systemic lupus erythematosis, PANDAS, rheumatic fever, sarcoidosis, Sjorgren syndrome, Stiff-Man syndrome, scleroderma, Wegener's granulomatosis, vitiligo, Wegener's disease, inflammatory bowel disease, idiopathic thrombocytopenic purpura (ITP), thrombotic throbocytopenic purpura (TTP), autoimmune thrombocytopenia, multiple sclerosis, psoriasis, IgA nephropathy, IgM polyneuropathies, myasthenia gravis, vasculitis, diabetes mellitus, Reynaud's syndrome, Sjorgen's syndrome and glomerulonephritis, autoimmune enteropathy, Goodpasture syndrome, dermatomyositis, polymyositis, autoimmune allergy, asthma and autoimmune reaction after organ transplantations.

Amounts effective will depend, of course, on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation. It is generally preferred that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reason.

In one embodiment of the invention, patients suffering from RA are administered xenon at a concentration of 25% xenon in 75% air. Various concentrations may be performed and adjusted based on immunological and clinical responses. In a preferred embodiment administration of xenon is performed 3 times per week in a volume of 10 liters, with a concentration of 25% xenon and 75% air. Other gases such as argon, helium, neon and krypton may be utilized. Additionally, other excipients may be added to alter immunological parameters. In order to guide of skill in the art in the practice of the invention, a table of some of the immunological intervention clinical trials for RA is provided below. This table may serve to guide a practitioner of the invention in choosing immunological and clinical parameters for assessment.

| Phase I/II Studies in RA | | | |
| --- | --- | --- | --- |
| Number of Patients | Experimental Drug | Endpoints | Reference |
| 20 | Antibody to TNF-alpha | Safety, morning stiffness, VAS pain scale, number of swollen joints, 5 point symptom scale, Health Assessment Questionnaire, Richie articular index | [20] |
| 30 | Antibody to IL-15 | Safety, tender joint count, swollen joint count, early morning stiffness, pain score (visual analog scale), patient global assessment, physician global assessment, Health Assessment Questionnaire, American College of Rheumatology Response Score | [21] |
| 8 | Autologous stem cell and cyclophosphamide | Safety, swollen joint count, duration of morning stiffness (in minutes), pain score using a 100-mm visual analog scale (VAS), disability section of the Health Assessment Questionnaire | [22] |
| 24 | Anti-CD4 antibody | Safety, American College of Rheumatology Response Score, RA-specific Health Assessment Questionnaire | [23] |
| 16 | Oral CCR1 antagonist | 28 joint count for joint swelling and tenderness, doctor's and patient's assessment of disease activity on a scale from 1 (asymptomatic) to 5 (severe symptoms), pain assessed by a visual analogue scale from 0 (no pain) to 100 (severe pain), quality of life (Health Assessment Questionnaire (HAQ)) from 0 (no disability) to 3 (severe disability) | [24] |

For monitoring RA disease activity for this rheumatoid arthritis trial, a 28-joint count for tenderness and swelling is employed. To assess the tender joint count, the examiner documents which joints the patient indicates are painful on palpation with enough pressure to blanch the nail bed of the examiner's thumb and index fingers. To assess the swollen joint count, the examiner documents which joints have palpable soft tissue swelling or fluctuance, excluding joints affected only by deformity or bony hypertrophy. The 28-joint count includes the shoulders, elbows, wrists, first to fifth metacarpophalangeal joints, first to fifth proximal interphalangeal joints, and knees on both sides of the body. Compared to more extensive joint counts, the 28-joint count has the advantage of being quick and easy to perform; however, it is limited by the fact that the ankles and metatarsophalangeal joints are not included, so active disease in the feet may be underestimated. The 28-joint count is used to calculate the disease activity score 28 (DAS28), which is a validated instrument to monitor disease activity.

This is performed as follows:

1. Perform a swollen and tender joint examination of your patient, noting each affected joint on Form A. When complete, add all of the swollen and tender joints and record the totals in the appropriate boxes on Form B.

2. Obtain and record the patient's erythrocyte sedimentation rate (ESR) in mm/h in the appropriate box on Form B. Note: C-reactive protein (CRP) levels may be used as a substitute for an ESR.

3. Obtain and record the patient's general health on a Visual Analog Scale (VAS) of 100 mm in the appropriate box on Form B. Note: DAS28 calculations may be performed without a VAS measurement.

4. Plug the appropriate values into the formula: DAS28=0.56*√(tender joints)+0.28*√(swollen joints)+0.70*Ln(ESR/CRP)+0.014*VAS 5. A DAS28 score of higher than 5.1 is indicative of high disease activity, whereas a DAS28 below 3.2 indicates low disease activity. A patient is considered to be in remission if they have a DAS28 lower than 2.6.

|  | Left | | Right | |
| --- | --- | --- | --- | --- |
|  | Swollen | Tender | Swollen | Tender |
| FORM A | | | | |
| Shoulder | | | | |
| Elbow | | | | |
| Wrist | | | | |
| Metacarpophalangeal | | | | |
| (MCP) 1 | | | | |
| 2 | | | | |
| 3 | | | | |
| 4 | | | | |
| 5 | | | | |
| Proximal Interphalangeal | | | | |
| (PIP) 1 | | | | |
| 2 | | | | |
| 3 | | | | |
| 4 | | | | |
| 5 | | | | |
| Knee | | | | |
| Subtotal | | | | |
| TOTAL | | | | |
|  | Total Swollen: | | Total Tender: | |
| FORM B | | | | |
| Swollen (0-28) | | | | |
| Tender (0-28) | | | | |
| ESR (or CRP) | | | | |
| VAS disease activity (0-100 mm) | | | | |

The EULAR response criteria include not only change in disease activity but also current disease activity. To be classified as responders, patients should have a significant change in DAS and also low current disease activity. Three categories are defined: good, moderate, and non-responders. EULAR response criteria combine the DAS28 score at the time of evaluation with the change in DAS28 score between two time points, and enable the user to define improvement or response to treatment. The thresholds for low disease activity and remission and the EULAR response criteria provide a standardised guide on how to interpret the DAS28 scores The HAQ was developed as a comprehensive measure of outcome in patients with a wide variety of rheumatic diseases, including rheumatoid arthritis, osteoarthritis, juvenile rheumatoid arthritis, lupus, scleroderma, ankylosing spondylitis, fibromyalgia, and psoriatic arthritis. It has also been applied to patients with HIV/AIDS and in studies of normal aging. It should be considered a generic rather than a disease-specific instrument. Its focus is on self-reported patient-oriented outcome measures, rather than process measures.

Thus, in one embodiment of the invention, therapeutic Noble Gas compositions are administered in a manner to alter immunological factors in the body. Specifically, the invention teaches that various concentrations of xenon gas, when delivered into circulation, either by inhalation [25-27], or administration of echogenic xenon liposomes [28, 29], can be utilized to induce a T regulatory cell phenotype and suppression of Th17 or other arthritogenic cells. The use of xenon has been reviewed by numerous authors in the art, which provide guidance as to details of administration [30-32]. Importantly, the new and non-obvious aspect of the current invention is that xenon, as well as other Noble gases, are capable of inducing immune modulation to inhibit autoimmunity, as well as to inhibit pain associated with RA.

Examples of gases or gas mixtures employed as medicament for radiation protection: 1.) 100% by volume xenon; 2.) 70% by volume xenon/30% by volume oxygen; 3.) 65% by volume xenon/30% by volume oxygen/5% by volume nitrogen; 4.) 65% by volume xenon/35% by volume oxygen; 5.) 60% by volume xenon/30% by volume oxygen/10% by volume nitrogen; 6.) 60% by volume xenon/35% by volume oxygen/5% by volume nitrogen; 7.) 60% by volume xenon/40% by volume oxygen; 8.) 55% by volume xenon/25% by volume oxygen/20% by volume nitrogen; 9.) 55% by volume xenon/30% by volume oxygen/15% by volume nitrogen; 10.) 55% by volume xenon/35% by volume oxygen/10% by volume nitrogen; 11.) 55% by volume xenon/40% by volume oxygen/5% by volume nitrogen; 12.) 55% by volume xenon/45% by volume oxygen; 13.) 50% by volume xenon/50% by volume oxygen; 14.) 50% by volume xenon/45% by volume oxygen/5% by volume nitrogen; 15.) 50% by volume xenon/40% by volume oxygen/10% by volume nitrogen; 16.) 50% by volume xenon/30% by volume oxygen/20% by volume nitrogen; 17.) 50% by volume xenon/25% by volume oxygen/25% by volume nitrogen; 18.) 45% by volume xenon/55% by volume oxygen; 19.) 45% by volume xenon/50% by volume oxygen/5% by volume nitrogen; 20.) 45% by volume xenon/45% by volume oxygen/10% by volume nitrogen; 21.) 45% by volume xenon/40% by volume oxygen/15% by volume nitrogen; 22.) 45% by volume xenon/35% by volume oxygen/20% by volume nitrogen; 23.) 45% by volume xenon/30% by volume oxygen/25% by volume nitrogen; 24.) 45% by volume xenon/30% by volume oxygen/25% by volume nitrogen; 25.) 40% by volume xenon/30% by volume oxygen/30% by volume nitrogen; 26.) 40% by volume xenon/50% by volume oxygen/10% by volume nitrogen; 27.) 35% by volume xenon/25% by volume oxygen/40% by volume nitrogen; 28.) 35% by volume xenon/65% by volume oxygen; 29.) 30% by volume xenon/70% by volume oxygen; 30.) 30% by volume xenon/50% by volume oxygen/20% by volume nitrogen; 31.) 30% by volume xenon/30% by volume oxygen/40% by volume nitrogen; 32.) 20% by volume xenon/80% by volume oxygen; 33.) 20% by volume xenon/30% by volume oxygen/50% by volume nitrogen; 34.) 15% by volume xenon/30% by volume oxygen/55% by volume nitrogen; 35.) 15% by volume xenon/50% by volume oxygen/35% by volume nitrogen; 36.) 10% by volume xenon/90% by volume oxygen; 37.) 10% by volume xenon/50% by volume oxygen/40% by volume nitrogen; 38.) 10% by volume xenon/30% by volume oxygen/60% by volume nitrogen; 39.) 10% by volume xenon/25% by volume oxygen/65% by volume nitrogen; 40.) 5% by volume xenon/25% by volume oxygen/70% by volume nitrogen; 41.) 5% by volume xenon/30% by volume oxygen/65% by volume nitrogen; 42.) 5% by volume xenon/50% by volume oxygen/45% by volume nitrogen; 43.) 5% by volume xenon/30% by volume oxygen/65% by volume nitrogen; 44.) 5% by volume xenon/95% by volume oxygen; 45.) 1% by volume xenon/99% by volume oxygen; 46.) 1% by volume xenon/30% by volume oxygen/69% by volume nitrogen; 47.) 1% by volume xenon/25% by volume oxygen/74% by volume nitrogen.

In an expanded use of the invention, a wider variety of autoimmune conditions may be treated, said conditions may be treated by said Noble gas containing compositions, or may be treated by combinations with existing immune modulator drugs and Noble gas containing compositions. In a more selected manner, the invention may be utilized by administration of antigen-specific tolerogenic vaccines with said Noble gas containing compositions. Autoimmune diseases include refers to any disease or disorder in which an immune response is generated in response to a substance, such as a protein or a tissue, that is normally present in the body and such response is undesirable. Generally, such a disease or disorder includes undesired immune responses to one or more self antigens. Autoimmune disease and autoimmune disorder may be used interchangeably through the disclosure and are considered to be synonymous. The list of autoimmune diseases may include, but is not limited to, multiple sclerosis, rheumatoid arthritis, type 1 diabetes, Crohns disease, ulcerative colitis, psoriasis, etc. Autoimmune diseases may also include diseases induced by foreign antigens, such as celiac disease. Non-limiting examples of autoimmune diseases also include Acute disseminated encephalomyelitis (ADEM), Addison's disease, Agammaglobulinemia, Alopecia areata, Amyotrophic lateral sclerosis, Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopenic purpura, Autoimmune uveitis, Behcet's disease, Celiac disease, Cold agglutinin disease, Crohn's disease, Dermatomyositis, Dermatomyositis, Diabetes mellitus type 1, Eosinophilic fasciitis, Goodpasture's syndrome, Graves' disease, Guillain-Barre syndrome (GB S), Hashimoto's encephalopathy, Hashimoto's thyroiditis, Idiopathic thrombocytopenic purpura, Lupus erythematosus, Miller-Fisher syndrome, Mixed connective tissue disease, Multiple sclerosis, Myasthenia gravis, Narcolepsy, Pemphigus vulgaris, Pernicious anaemia, Polymyositis Primary biliary cirrhosis, Psoriasis, Psoriatic arthritis, Relapsing polychondritis, Rheumatoid arthritis, Rheumatic fever, Sjogren's syndrome, Temporal arteritis, Transverse myelitis, Ulcerative colitis, Undifferentiated connective tissue disease, Vasculitis, and Wegener's granulomatosis. In some embodiments, the autoimmune disease is Multiple Sclerosis (MS). Generally, the autoimmune disease or disorder is T-cell-mediated.

EXAMPLE

Treatment of 20 DMARD-Resistant RA Patients with Xenon 20 patients with disease modifying antirheumatic drug (DMARD)-resistant Rheumatoid Arthritis (RA) are chosen for a clinical trial assessing safety and efficacy of 25% Xenon administration with 75% air. A total of 10 liters of gas inhaled. Administration is performed 3 times per week.

The number of 20 patients has been chosen based on previous clinical trials aiming to identify a signal of efficacy with demonstration of feasibility and safety [20-24].

Safety is determined by assessment of hematological biochemical, and coagulation parameters on baseline, and days 30, 60, and 90. Efficacy is assessed by CRP, ESR, anti-citrulline antibody, RF, Quality of Life Questionnaire, 28-joint disease activity score (DAS28), European League against Rheumatism (EULAR) response criteria and immunological parameters.

Men and women at least 18 years of age are eligible to participate if they meet the American College of Rheumatology (ACR) criteria for RA for at least one year and are in functional Class I, II, or III [33]. All patients will have to have had at least one failed trial of a DMARD and must have at least 10 painful and 10 swollen joints at entry. No DMARD therapy is allowed within 4 weeks of study entry. Patients receiving nonsteroidal anti-inflammatory drugs, corticosteroids (<10 mg per day), or both will be allowed in the trial if they have been on stable doses for at least four weeks before study entry. Required baseline laboratory values include serum creatinine and blood urea nitrogen<1.5× the upper limit of normal and alanine aminotransferase and aspartate aminotransferase<2.0× the upper limit of normal. Exclusionary laboratory values include a platelet count of >500,000/mm3, hematocrit<30%, and a white-blood-cell count<3000/mm3. Other exclusionary criteria include history of cancer, use of intravenous or intraarticular corticosteroids within four weeks of randomization, any prior use of cyclosporine or cyclophosphamide, use of any investigational agent within 30 days of study entry, severe extra-articular manifestations of RA, acute infection requiring antibiotic therapy within two weeks of study entry, other concurrent autoimmune disease (e.g. systemic lupus erythematosus), or any other condition that the investigator thought might have placed the patient at undue risk if they had participated in the trial. Men and women of childbearing potential are to use approved methods of birth control. Women have to have a negative result on a test of serum beta human chorionic gonadotropin at screening. Medications including cyclosporine, cyclophosphamide, and any DMARD will not allowed. The use of intravenous or intraarticular corticosteroids will not be permitted. The following analgesics are permitted: acetaminophen, acetaminophen with codeine, acetaminophen with oxycodone, and propoxyphene. Patients will be instructed not to take analgesics within 12 hours of their planned study visit.

The primary objective of this feasibility study is to provide clinical data to demonstrate the safety and efficacy of xenon administration 10 liters at 25% xenon, 3 times per week for the duration of the trial in treating patients diagnosed with DMARD-resistant rheumatoid arthritis (RA).

The secondary objectives are to demonstrate that xenon administration impacts the clinical course of RA resistant to DMARDS as measured by QOL questionnaire, 28 joint DAS and EULAR criteria, and to assess the effect of the xenon therapy on immunological/inflammatory parameters including CRP, RF, anti-citrulinated antibodies.

Safety will be assessed throughout the study with the use of direct evaluation and patient reporting during study visits or patient-initiated telephone contacts. The types, frequencies, severity, and duration of any reported adverse event or abnormalities in clinical laboratory values, physical examinations, vital signs, or special cardiovascular evaluations will be assessed. The changes from baseline will be summarized.

Safety data to be summarized include by not limited to:
Adverse Events/Serious Adverse Events
Complete blood count
Physical assessment/vital signs
ECG To assess preliminary evidence of efficacy, the following assessments will be analyzed at following time points and compared to baseline values:
Disease Severity at 1, 2, and 3 Months:
Changes in 28-joint disease activity score (DAS28)
Changes in European League against Rheumatism (EULAR) response criteria
Reduction in RF, ESR, CRP and anti-citrulinated fibrinogen antibody
Quality of Life Assessment at 1, 2, and 3 Months Measured by:
Change in Rheumatoid Arthritis Quality of Life (RAQoL) questionnaire Subsequent to therapy, patients demonstrate no significant treatment associated adverse events and reduction of clinical and immunological parameters of RA is noted in a statistically significant manner.

The invention claimed is:

1. A method of treating rheumatoid arthritis comprising the steps of: a) identifying a patient suffering from rheumatoid arthritis, and b) providing to said patient a noble gas composition comprising 25-30% xenon and 70-75% of air or oxygen by total volume of the noble gas composition in an amount sufficient to treat one or more symptoms of rheumatoid arthritis.

2. The method of claim 1, wherein said one or more symptoms of rheumatoid arthritis is selected from the group consisting of morning stiffness, painful joints, swollen joints, loss of grip strength, and pain.

3. The method of claim 1, wherein said noble gas composition consists essentially of a) oxygen and xenon or b) air and xenon.

4. The method of claim 1, wherein said noble gas composition further comprises a gas selected from the group consisting of nitrogen, helium, nitric oxide, krypton, argon and neon.

5. The method of claim 1, wherein said treatment of one or more symptoms is assessed using a European League Against Rheumatism score.

6. The method of claim 1, wherein said treatment of one or more symptoms is assessed using quantification of levels of inflammatory markers.

7. The method of claim 6, wherein said inflammatory marker is selected from the group consisting of a) c-reactive protein; b) interleukin-1; c) interleukin-6; d) interleukin-8; e) interleukin-17; f) tumor necrosis factor-alpha; g) high-mobility group box 1 protein; and h) interleukin-33.

8. A method of increasing sensitivity to an anti-cytokine biologic treatment in a rheumatoid arthritis patient, comprising:
identifying a patient suffering from rheumatoid arthritis; and
providing to said patient a noble gas composition comprising 25-30% xenon and 70-75% of air or oxygen by total volume of the noble gas composition in an amount sufficient to increase sensitivity to said anti-cytokine biologic treatment.

9. A method of inducing self-antigen specific tolerance in a rheumatoid arthritis patient, comprising:
identifying a patient suffering from rheumatoid arthritis and having an intolerance to a self-antigen; and
providing to said patient a noble gas composition comprising 25-30% xenon and 70-75% of air or oxygen by total volume of the noble gas composition in an amount sufficient to induce tolerance to said self-antigen.

* * * * *